United States Patent [19]

Shimozono

[11] Patent Number: 5,042,938
[45] Date of Patent: Aug. 27, 1991

[54] APPARATUS FOR MEASURING LENGTH OF VISUAL LINE LENGTH, DEPTH OF ANTERIOR CHAMBER, THICKNESS OF CRYSTAL LENS, ETC.

[75] Inventor: Hiroaki Shimozono, Tokyo, Japan

[73] Assignee: Kabushiki Kaisha TOPCON, Japan

[21] Appl. No.: 520,201

[22] Filed: May 3, 1990

[30] Foreign Application Priority Data

May 9, 1989 [JP] Japan .................................. 1-115838
May 9, 1989 [JP] Japan .................................. 1-115839

[51] Int. Cl.$^5$ .............................................. A61B 3/10
[52] U.S. Cl. .................................... 351/205; 351/211; 351/221
[58] Field of Search ............... 351/205, 206, 211, 221; 356/382; 128/665, 745, 774

[56] References Cited

U.S. PATENT DOCUMENTS 4,820,037 4/1989 Kohayakawa ...................... 351/211

OTHER PUBLICATIONS

A. F. Fercher et al., Optics Letter, vol. 13, No. 3, pp. 186–188, Mar. 1988, Optical Society of America, "Eye-Length Measurement by Interferometry with Partially Coherent Light".

Primary Examiner—Rodney B. Bovernick
Attorney, Agent, or Firm—Finnegan, Henderson, Farabow, Garrett & Dunner

[57] ABSTRACT

A measuring apparatus has a model eye for measuring a distance from a first objective surface to a second objective surface, an observation optical system for observing an interference between reflected light flux from the model eye and reflected light flux from the object eye, and a light flux split member for splitting light flux and guiding coherent split light flux to both the object eye and the model eye. The model eye is provided with at least a first surface corresponding to the first objective surface and a second surface corresponding to the second objective surface. The interference fringe between the first surface and the first objective surface being observed, and the interference fringe between the second surface and the second objective surface is in order to measure the length of a visual line as a distance from the first objective surface to the second objective surface (eye axial length), the depth of the anterior chamber, the thickness of a crystal lens, etc.

10 Claims, 5 Drawing Sheets

APPARATUS FOR MEASURING LENGTH OF VISUAL LINE LENGTH, DEPTH OF ANTERIOR CHAMBER, THICKNESS OF CRYSTAL LENS, ETC.

BACKGROUND OF THE INVENTION

1. Field of the Invention

This invention relates to an apparatus for measuring a visual line length, a distance from a first objective surface of an eye ball to a second objective surface, and particularly to an apparatus for measuring an eye axial length, the depth of an anterior chamber, the thickness of the crystal lens, etc. in a noncontact style.

2. Description of the Prior Art

Heretofore, there has been an apparatus using a supersonic wave as an apparatus for measuring a visual line length as a distance from a first anterior face of an eye ball to a second rear face thereof an eye axial length, the depth of an anterior chamber, the thickness of a crystal lens, etc. The supersonic wave is projected toward the eye.

And this supersonic wave is reflected by an anterior face of cornea, an anterior face of crystal lens, a rear face of crystal lens, and a surface of retina. These echoes are drawn on a Braun tube or CRT. Echogram drawn on the CRT is taken for measurement.

However, as the measurement accuracy of the visual line length of this conventional apparatus is about ±0.2 mm, such measured value is not enough to use for determining power of, for example, IOL (intraocular lens).

Also, as a probe is contacted with the eye when the eye is measured with this conventional apparatus using a supersonic wavelength is necessary to take some measures for avoiding infection.

Therefore, in a recent year, there was proposed an apparatus for measuring the visual line length, in a noncontact style by observing an interference fringe.

One such example is depicted in FIG. 6. This apparatus is used for measuring the visual line length. This apparatus is described in A. F. Fercher et al. (OPTICS LETTER VOL. 13 NO.3 PP.186-188 (MAR. 1988) Optical Society of America).

The apparatus of FIG. 6 generally comprises a semiconductor laser 1, a collimate lens 2, a couple of parallel planes 3, 4, a beam splitter 5, a condenser lens 6, and an image pick up device type camera 7. Laser beam emitted from the semiconductor laser 1 is made into a parallel flux of light rays by the collimate lens 2. The parallel flux of light rays pass through the couple of parallel planes 3, 4. The parallel flux of light rays (hereinafter referred to as "light flux ①"), which have passed through the couple of parallel planes 3, 4 are guided to an eye 8 through a beam splitter 5. And the light flux ① are made into a convergent light by the function of the eye 8. The convergrent light reaches a retina 9. This convergent light is reflected by the retina 9. The reflected light is emitted from the eye 8 in the form of generally parallel flux of light rays (plane wave). The light flux ① coming from the eye 8 is reflected by a reflecting surface 10 of the beam splitter 5 in the direction where the condenser lens 6 is placed. The condenser lens 6 condenses the light flux reflected by the reflecting surface 10. The light flux passed through the condenser lens 6 reaches the image pick up device type camera 7.

Also, a part of the light flux ① passed through the parallel plane 3 is reflected by the parallel plane 4. The reflected light flux (hereinafter referred to as the "light flux" ②) are returned to the parallel plane 3 and passed through this parallel plane 4. The light flux ② passed through the parallel plane 4 are passed through the beam splitter 5 and guided to a cornea 11. Then, the flux ② are reflected by the cornea 11. The reflected light from the cornea 11 is guided to the beam splitter 5 in the form of divergence beam (spherical wave). The divergence beam is reflected by the reflecting surface 10 to reach the condenser lens 6. The divergence beam is condensed by the condenser lens 6 and reaches the camera 7. In FIG. 6, the numeral 12 denotes a sensor for monitoring amount of light of the semiconductor laser 1.

In this conventional apparatus, a distance 1 between the parallel planes 3 and 4 can be changed. If the refractive index of a substance existing between the parallel planes 3 and 4 is represented by n, the refractive index of an intraocular material is represented by N, and the measured value (distance from the apex of the cornea 11 to the retina 9) of the visual line length is represented by X, the distance 1 between the parallel planes 3 and 4 is adjusted in such a manner as to satisfy the following equation.

$$n \cdot l = N \cdot X$$

Then, an optical path length of the light flux ① and an optical path length of the light flux ② become equal.

Therefore, the interference fringe is observed by using the camera 7. By obtaining the position (distance l) of the parallel plane as a measured value at the time when this interference fringe is observed, the visual line length X can be found.

The apparatus for measuring the visual line length by observing this interference fringe has light flux reflected from the outer surface of the cornea is a generally spherical wave. On the other hand, the light flux reflected from the the surface of the retina is a generally plane wave. Therefore, the number of stripes of the interference fringe is greatly increased as it goes away to the marginal portion from the apex of the cornea and the interference fringe cannot be favorably observed. Furthermore, in this conventional apparatus, it is very troublesome in order to align the optical axes of the condenser lens 6 and the camera 7 with respect to the eye 8.

SUMMARY OF THE INVENTION

A first object of the present invention is to provide an apparatus for measuring the length of a visual line length, for example an eye axial length, the depth of anterior chamber, the thickness of crystal lenses in which the interference fringe can be observed with ease without performing a very accurate alignment with respect of the eye and the improvement of the measurement accuracy can be much expected.

An measuring apparatus for achieving this first object, includes:
- a model eye for measuring a distance from a first objective surface of an object eye to a second objective surface of the object eye;
- an observation optical system for observing an interference between reflected light flux from said model eye and reflected light flux from said object eye; and a light flux split member for splitting light flux and guiding coherent split light flux to both said object eye and said model eye;

said model eye being provided with at least a first surface corresponding to said first objective surface of eye and a second surface corresponding to said second objective surface of object eye;

said interference fringe between said first surface and said first objective surface being observed, and said interference fringe between said second surface and said second objective surface being observed, in order to measure the length of a visual line as a distance from said first objective surface to said second objective surface, the depth of said anterior chamber, the thickness of a crystal lens, etc.

According to an apparatus of this first invention, a reflected wave from said first surface and a reflected wave from said first objective surface are generally the same in wave configuration. Similarly, a reflected wave from said second surface and a reflected wave from said second objective surface are also generally the same. Therefore, light flux having the same wave surface configuration are interfered with each other to form an interference fringe. There can be obtained an interference fringe which is desirable to observe. The interference fringe can be easily and favorably obtained without performing alignment with respect to the object eye.

A second object of the invention is to provide a measuring apparatus in which when the length of a visual line length, for example an eye axial length, the depth of an anterior chamber, the thickness of a crystal lens, etc. are measured by obtaining an interference fringe using a model eye, contrast of said interference fringe is favorable.

A measuring apparatus in order to achieve the second object is designed such that in the measuring apparatus according to the present invention, an optical member for regulating a mount of light is disposed between the light flux split member and the model eye.

According to this second invention, when the contrast of such obtained interference fringe is low, the contrast of the interference fringe becomes favorable if the optical member for regulating a mount of light is adjusted.

DETAILED DESCRIPTION OF THE EMBODIMENT

Embodiment 1

Figure 1:
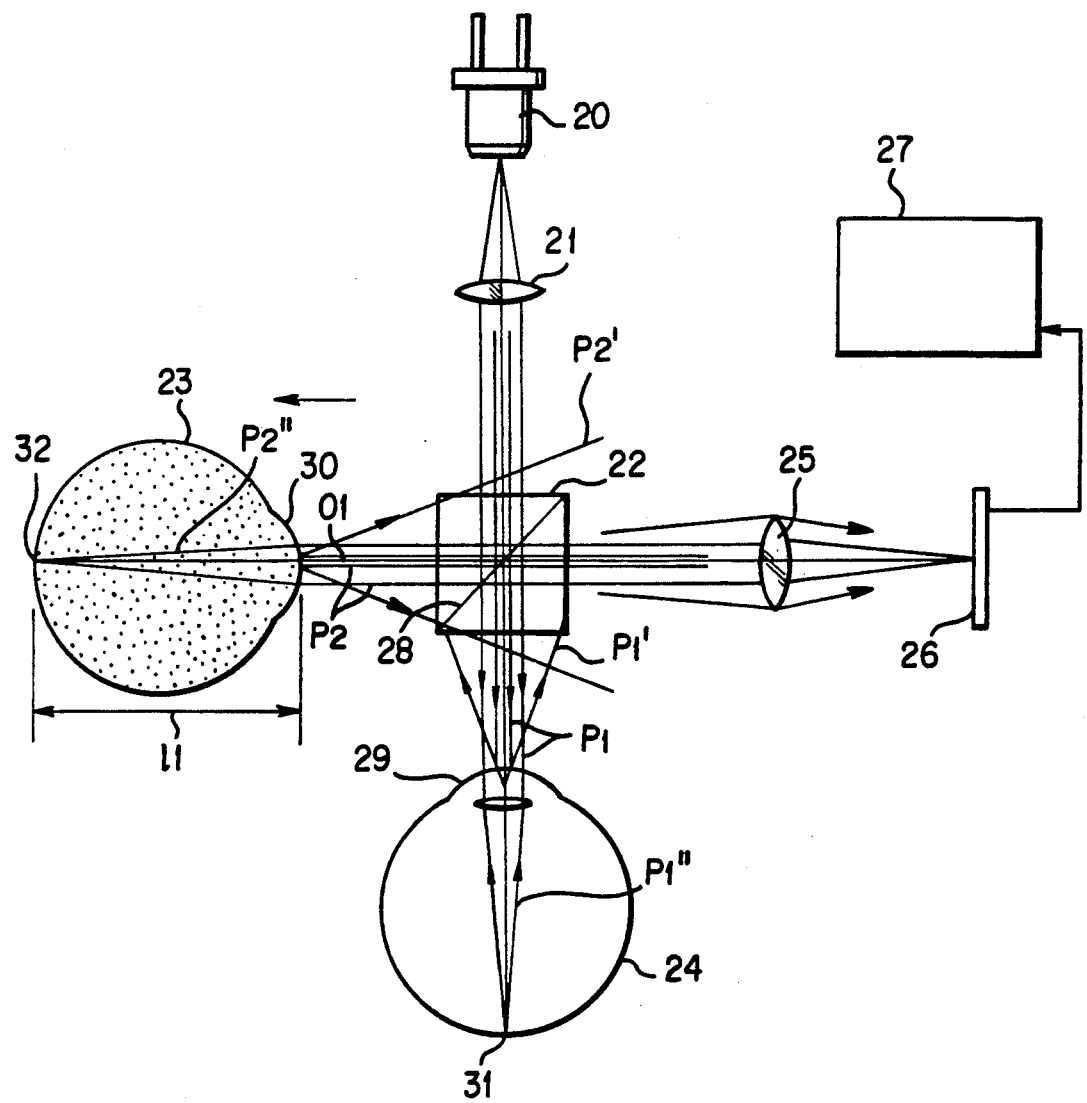
FIG. 1 is a view showing an optical system of a first embodiment of the present invention.

FIG. 1 is an optical system showing the first embodiment of the present invention. The optical system of the measuring apparatus shown in FIG. 1 is used for measuring a visual line length here.

In FIG. 1, the numeral 20 denotes a semiconductor laser, 21 a collimate lens, 22, a beam splitter, 23 a model eye, 24 an eye of a creature (for example, an eye of a human being), 25 a condenser lens forming a part of an observation optical system, 26 a CCD camera, and 27 a TV monitor.

The coherent length of the semiconductor laser 20 used here is 0.1 mm or less. The reason for this choice is as follows.

That is, if the coherent length of the semiconductor laser 20 is 1 mm or more, presuming that an interference fringe can be observed when the model eye 23 is in a position situated in the direction of an optical axis as will be described later, a slight movement of the model eye 23 from that position does not make the interference fringe disappear. Therefore, the requirement that the measurement accuracy of the apparatus is about 0.1 mm is not satisfied.

On the other hand, if the coherent length of the semiconductor laser 20 is made short, the measurement accuracy is improved. However, it is not desirable that the coherent length of the semiconductor laser 20 is extremely short. The reason is that the interference fringe is difficult to obtain. Moreover, it is another reason that it takes a long time for measurement.

Particularly, an interference fringe based on interference between a retina and a second surface as will be described later becomes complicated in configuration. The reason is that the configuration of the retina is complicated. Therefore, when the coherent length of the semiconductor laser 20 is extremely short, it is not an easy to make a judgment whether the interference fringe is obtained or not.

Laser beam emitted from the semiconductor laser 20 is made into a parallel light flux by the collimate lens 21. The parallel light flux is split into a parallel light flux P1 and another parallel light flux P2.

The model eye 23 has a first surface 30 and a second surface 32. The first surface 30 is in correspondence with a cornea 29 as a first objective surface. The second surface 32 is in correspondence with a retina 31 as a second objective surface.

A value of the radius of curvature of an average retina 29 of a human being is used as a value of the radius of curvature of the first surface 30. The radius of curvature of the first surface 30 is 7~8 mm here. Also, a value of the radius of curvature of an average retina 31 of a human being is used as a value of the radius of curvature of the second surface 32. Furthermore, the refractive index n of the model eye 23 is almost equal to the refractive index N of an intraocular material. An average value of the visual line length of the eye 24 is a distance from the first surface 30 to the second surface 32. The distance l is 22 mm ~ 24 mm here. In order to make the parallel light flux entered into the model eye 23 converge to the second surface 32, the distance l the radius of curvature of the first surface 30, the radius of curvature of the second surface 32, and the refractive index n are selected respectively. The model eye 23 is movable in the direction of an optical axis O1.

Reflected light flux from the cornea 29 and the first surface 30 is made into a light flux (wave surface resembling to a spherical wave) resembling to a divergent light flux. On the other hand, a reflected light flux from the retina 31 and a reflected light flux from the second surface are made into light flux (wave surface resembling to plane wave) respectively when they are emitted from the cornea 29 and the first surface 30.

The model eye 23 is now moved in the direction of the optical axis O1 so that the model eye 23 is conjugate with the cornea 29 of the eye 24 with reference to the reflected surface 28 of the beam splitter 22. Then, light flux P2' reflected by the first surface 30 and light flux P1' reflected by the cornea 29 are condensed by the condenser lens 25 and guided to the CCD camera 26. An interference image based on the light flux P1' and P2' appears on the TV monitor 27.

Also, the model eye 23 is moved in the direction of the optical axis O1 so that the model eye 23 is conjugate with the retina 31 of the eye 24 with respect to the reflecting surface 28 of the beam splitter 22. Then, an interference fringe based on the the light flux P2" reflected by the second surface 32 and the light flux P1" reflected by the retina 31 is likewise appears on the TV monitor 27.

If the visual line length of the eye 24 is represented by X, the position of the model eye 23 in the direction of the optical axis O1 when the interference fringe is obtained based on the cornea 29 and the first schematic surface 30 is represented by X1, and the position of the model eye 23 in the direction of the optical axis O1 when the interference fringe is obtained based on the retina 31 and the second surface 32 is represented by X2, the following equation can be obtained.

$$N \cdot X = (X1 - X2) + n \cdot l$$

Therefore, by transfiguring the above equation, the following equation can be obtained.

$$X = \frac{(X1 - X2) + n \cdot l}{N}$$

The visual line length can be found using this equation.

According to an apparatus for measuring the length of visual line of the eye, etc. by measuring the interference fringe using this model eye 23, the wave configurations of light flux which causes the interference are almost same. Therefore, the number of the stripes of the interference fringe becomes appropriate and the interference fringe can be observed in satisfactory condition.

Embodiment 2

By the way, in case of the measuring apparatus shown in the first embodiment, the amount of light of reflected light flux from the first surface with respect to the amount of light of the reflected light flux from the first objective surface, and the amount of light of the reflected light flux from the second surface with respect to the amount of light of the reflected light flux from the second objective surface are extremely different, it is difficult to obtain an interference fringe having a favorable contrast.

Naturally, the contrast of the interference fringe becomes the best when the intensity of the amount of light of the light flux mutually interfered is equal.

Figure 2:
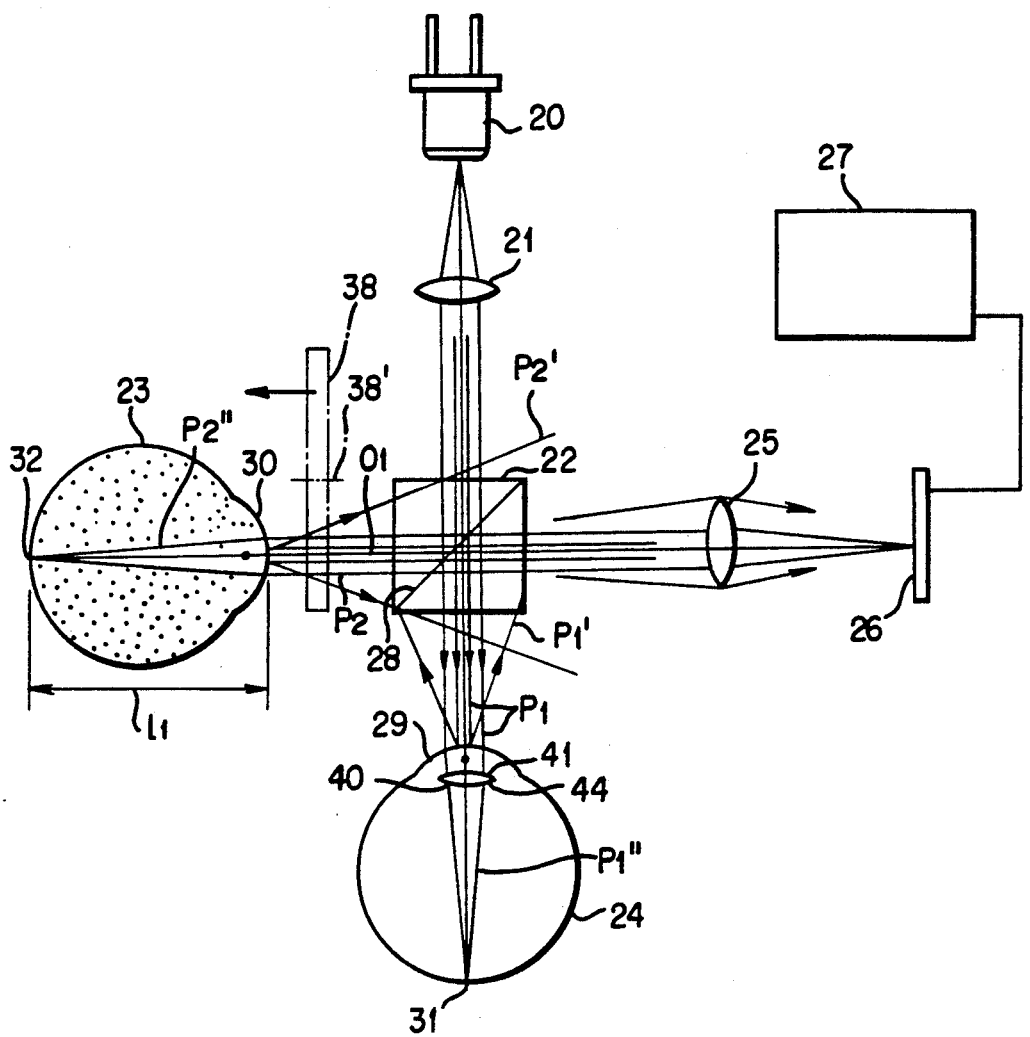
FIG. 2 is a view showing an optical system of a second embodiment of the present invention.

The embodiment trying to improve the contrast of the interference fringe is shown in FIG. 2.

Figure 3:
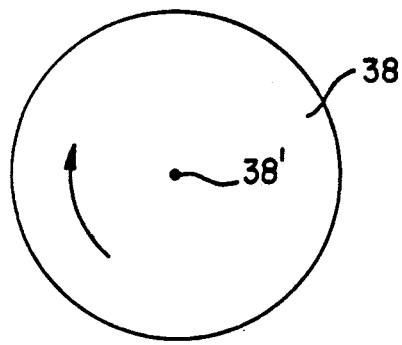
FIG. 3 is a plan view of the optical member for regulating a mount of light shown in FIG. 2.

FIG. 2 depicts a second embodiment, wherein an optical member for regulating an amount of light 38 is disposed between the model eye 23 and the beam splitter 22. A neutral density variable filter is used as this optical member for regulating an amount of light 38. The optical density variable filter is variable in density in the direction as shown by an arrow of FIG. 3. The reflection factor of the retina 29 of the eye 24, the transmittance of the crystal lens and the vitreous body are individually different depending on eyes. If the reflected light flux from the retina 31 of the eye 24 and the reflected light flux from the model eye 23 are extremely different here, contrast of the interference fringe is greatly degraded. Therefore, in order to obtain a favorable contrast of the interference fringe, the amount of light regulating optical member 38 is rotated about its axis 38', so that the amount of light of the reflected light flux from the first and second surfaces 30 and 32 of the model eye 23 comes close to the amount of light of the reflected light flux from the eye 24.

That is, if the contrast of this interference fringe is low when the interference fringe based on the light flux P1' and P2' appears on the TV monitor 27, the amount of light regulating optical member 38 is rotated about the axis 38' in order to obtain a favorable contrast. Also, the model eye 23 is moved in the direction of the optical axis O1 so that second surface 32 is conjugate with the retina 31 of the eye 24 of a creature with respect to the reflecting surface 28 of the beam splitter 22. Then, the interference fringe based on the light flux P2" reflected by the second surface 32 and the light flux P1" reflected by the retina 31 is likewise appeared on the TV monitor 27. In case the contrast of this interference is low, the amount of light regulating optical member 38 is also rotated about its axis 38' in order to obtain a favorable contrast.

Thus, according to this embodiment, the contrast of the interference fringe becomes favorable.

Embodiment 3

Figure 4:
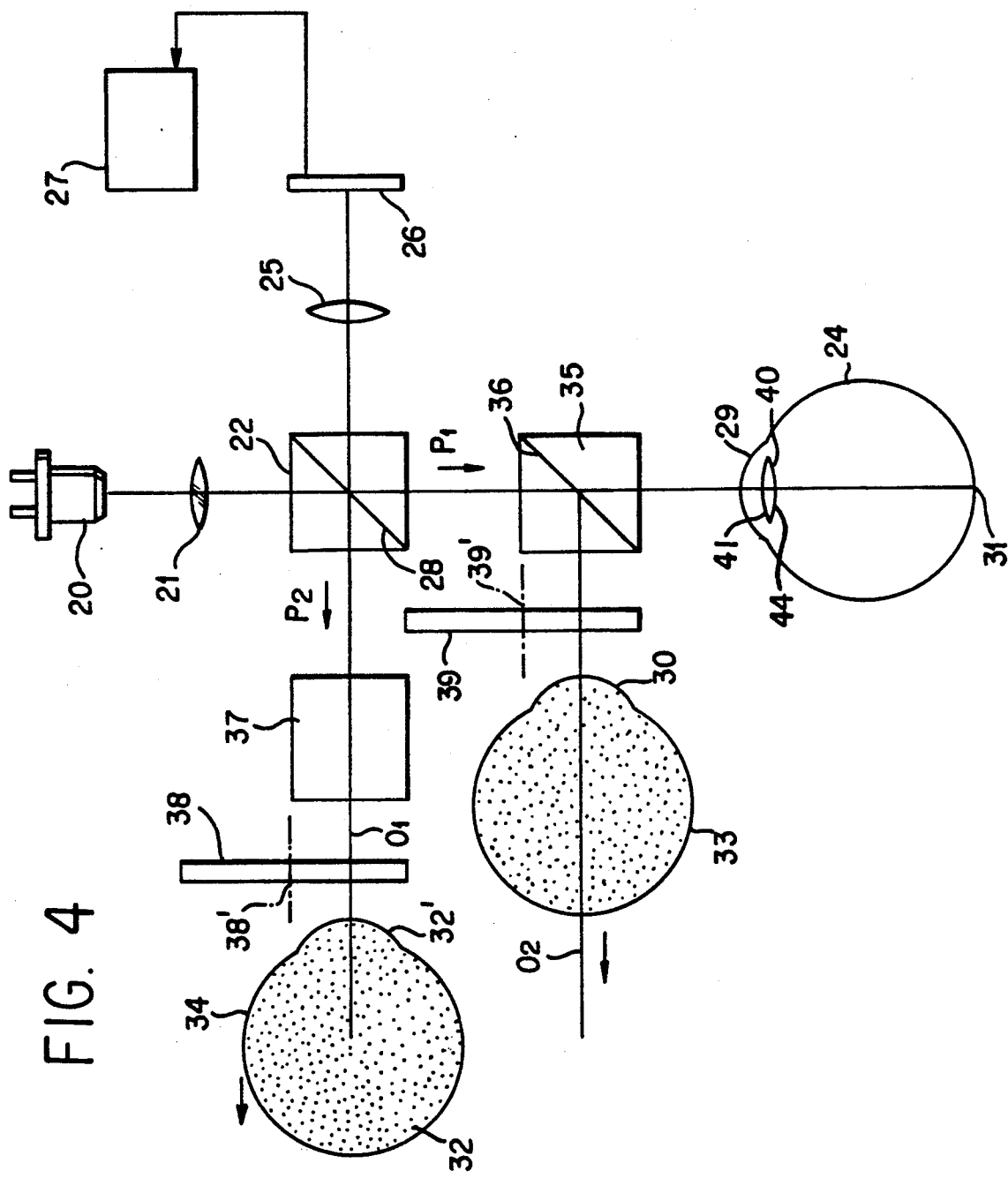
FIG. 4 is a view showing an optical system of a third embodiment of the present invention.

This third embodiment shows a case wherein the length of visual line is measured using a pair of model eyes which are individually separated optical substances. In FIG. 4, the numerals 33, 34 denote a pair of model eyes. The model eye 33 includes a first surface 30 which is in correspondence with the cornea 29 of the eye 24. The other model eye 34 includes a second surface 32 which is in correspondence with the retina 31 of the eye 24. A beam splitter 35 for splitting the split light flux P1 to be guided to the eye 24 into a light flux to be guided to the model eye 33 and a light flux to be guided to the eye 24 is disposed between the beam splitter 32 and the eye 24. The numeral 36 denotes the reflecting surface of the beam splitter 35. Between the model eye 34 and the beam splitter 22, an optical path length correcting optical member 37 is disposed in a position conjugated with the beam splitter 35 with respect to the reflecting surface 28 of the beam splitter 22.

The optical path length correcting optical member 37 has a substantially same configuration and a substantially same thickness and a substantially same refractive index as those of the beam splitter 35. The optical path length correcting optical member 37 has such function as to make an optical distance from the model eye 34 to the reflecting surface 28 of the beam splitter 22 substantially equal to an optical path from the model eye 33 to the reflecting surface 28 of the beam splitter 22 via the beam splitter 35.

The model eye 34 is provided with a antireflection film formed on its surface 32'. This antireflection film is adapted to reduce reflection of the split light flux P2" to be made incident to the model eye 34 on the surface 32'.

Between the model eye 34 and the beam splitter 35, an amount of light regulating optical member 38 like that of the second embodiment is disposed. Between the model eye 33 and the beam splitter 35, an amount of light regulating optical member 39 is disposed. This amount of light regulating optical member 39 has the substantially same construction as that of the amount of light regulating optical member 38. The amount of light regulating optical member 39 is also rotated about its axis 39' in order to obtain a favorable contrast when the contrast is low. However, when the amount of light of the reflected light flux from the cornea 29 and the amount of light of the reflected light flux from the first surface 30 are not substantially different and the contrast is favorable, it is not necessary to provide this amount of light regulating optical member 39 between the model eye 33 and the beam splitter 35.

The model eyes 33 and 34 are movable in the directions of the optical axes O1 and O2 simultaneously. When the first surface 30 of the model eye 33 and the cornea 29 are generally conjugate with each other, an interference fringe based on the model eye 33 appears on the TV monitor 27. When the contrast of the interference fringe obtained is based on the model eye 34, the amount of light regulating optical member 38 is rotated about its axis 38' in order to obtain a favorable contrast as in the case with the second embodiment.

In the case of this embodiment, when a known visual line length X2 is measured, the position of the model eye 33 in the direction of the optical axis O2 is represented by X10, and the position of the model eye 34 in the direction of the optical axis O1 is represented by X20. Also, if the positions of the model eyes 33, 34 in the direction of the optical axes O1, O2, when an unknown visual line length X of the eye 24 are measured, are respetively represented by X3 and X4, the following equation can be obtained.

$$(X3 - X10) + n \cdot (X4 - X20) = N \cdot (X - X0)$$

The character n denotes the refractive index of the model eye 34.

By this, an unknown visual line length X can be found.

According to this third embodiment, as the interference fringe obtained by the cornea 29 and the interference fringe obtained by the retina 31 appears on the TV monitor 27 simultaneously by moving the model eyes 33 and 34 simultaneously, the measuring time can be shortened when compared with the first and second embodiment.

Embodiment 4

Figure 5:
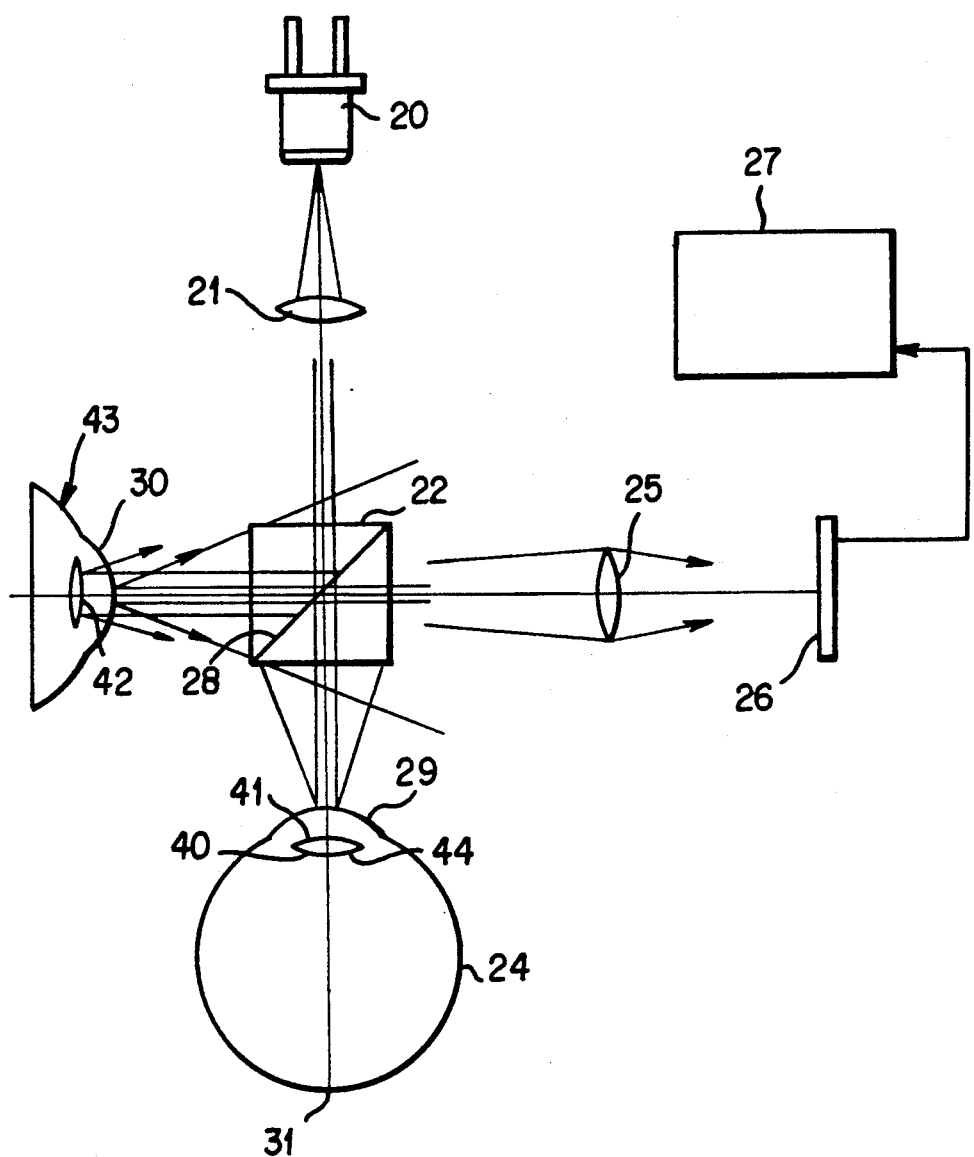
FIG. 5 is a view showing an optical system of a fourth embodiment.
Figure 6:
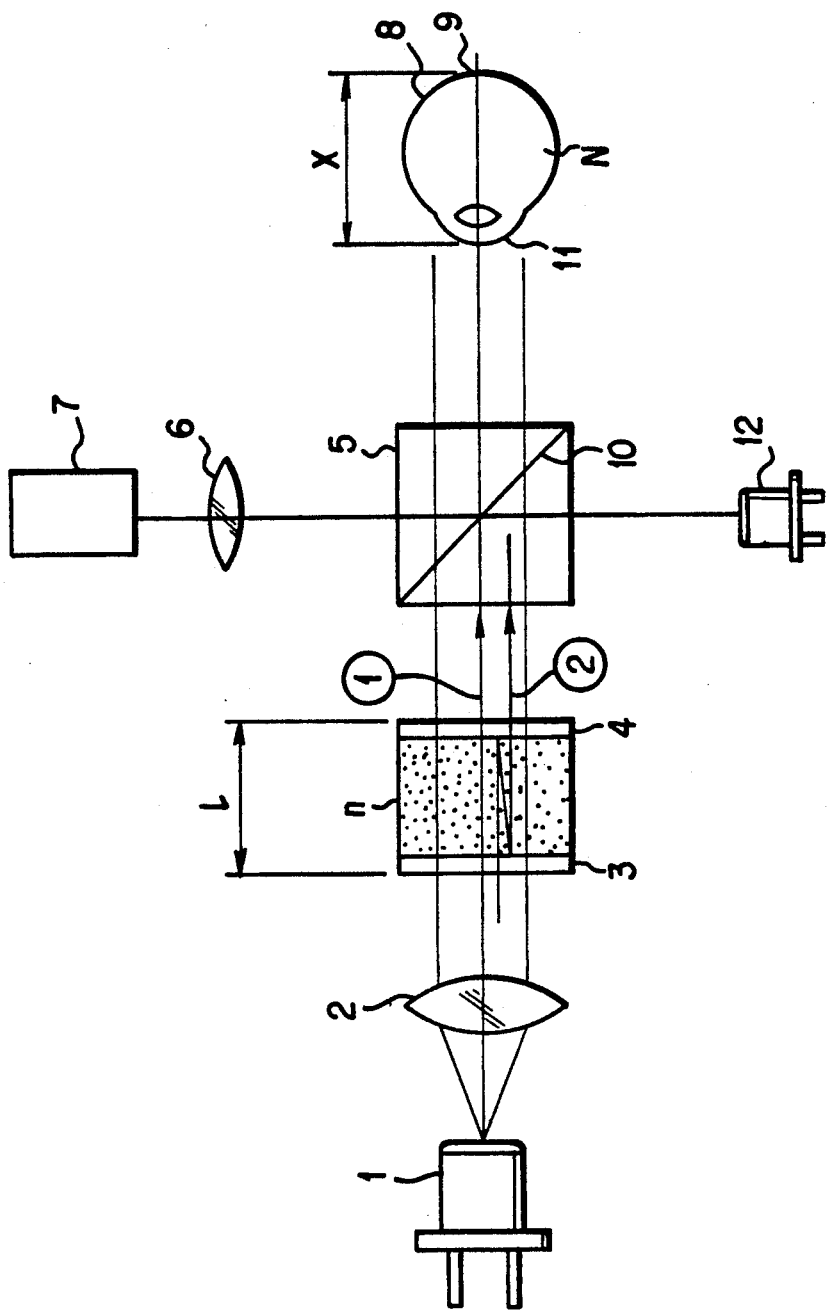
FIG. 6 is a view showing an optical system of a conventional apparatus for measuring the length of visual line, etc.

FIG. 5 shows a fourth embodiment of the present invention, which is used for measuring the depth of anterior chamber. In this fourth embodiment, a model eye 43 including a first surface 30 which is in correspondence with the cornea 29 of theeye 24 and a second surface 42 which is in correspondence with an anterior face 41 of a crystal lens 40 is used. According to this fourth embodiment, the depth of anterior chamber can be measured by observing the interference fringe based on the cornea 29 and the first surface 30, and by observing the interference fringe based on the second surface 42 and the anterior face 41 of crystal lens 40.

Although several embodiments have been described in the foregoing, if the interference fringe is observed by using a model eye including the first surface which is in correspondence with the anterior face 41 of the crystal lens 40 and the second surface which is in correspondence with the rear face 44 of the crystal lens 40, the thickness of the crystal lens from the anterior face 41 of the crysal lens 40 to the rear surface 44 can be measured.

Furthermore, if the model eye including the first surface which is in correspondence with the cornea 29 and the second surface which is in correspondence with the anterior face 41 of the crystal lens 40 is used, the depth of anterior chamber can be measured from the cornea 29 to the anterior face 41 of the crystal lens 40.

What is claimed is:

1. A measuring apparatus including:
   a model eye for measuring a distance from a first objective surface of an object eye to a second objective surface of the object eye;
   an observation optical system for observing an interference between reflected light flux from said model eye and reflected light flux from said object eye; and
   a light flux split member for splitting light flux and guiding coherent split light flux to both said object eye and said model eye;
   said model eye being provided with at least a first surface corresponding to said first objective surface and a second surface corresponding to said second objective surface;
   said interference fringe between said first surface and said first objective surface being observed, and said interference fringe between said second surface and said second objective surface being observed, in order to measure the length of a visual line as a distance from said first objective surface to said second objective surface, the depth of the anterior chamber, the thickness of a crystal lens.

2. A measuring apparatus including:
   a model eye for measuring a visual line length from the apex of the cornea of an object eye to a retina of the object eye;
   an observation optical system for observing an interference between reflected light flux from said model eye and reflected light flux from said object eye; and
   a light flux split member for splitting light flux and guiding coherent split light flux to both said object eye and said model eye;
   said model eye being provided with at least a first surface corresponding to the surface of said cornea and a second surface corresponding to said retina of said object eye;
   said interference fringe between said first surface and said surface of said cornea being observed, and said interference fringe between said second surface and the surface of said retina being observed, in order to measure the length of a visual line from said surface of said cornea to said surface of said retina.

3. A measuring apparatus according to claim 2, wherein said first surface is formed in such a manner as to be in generally correspondence with the curvature of said surface of said cornea and said second surface is formed in such a manner as to be in generally correspondence with the curvature of said surface of said retina.

4. A measuring apparatus according to claim 2, wherein said first surface and said second surface of said model eye are integrally formed using an optical substance, the refractive index of said optical substance being generally equal to the refractive index of an intraocular material of said object eye.

5. A measuring apparatus according to claim 2, wherein said model eye includes a first optical substance having said first surface and a second optical substance having said second surface, said first and second optical substances being individually separated bodies.

6. A measuring apparatus according to claim 2, wherein said light flux is emitted from a semiconductor laser and is split by said light flux split member and guided to said model eye and said object eye, respectively, 7. A measuring apparatus according to claim 6, wherein the coherent length of said semiconductor laser is 0.1 mm or less.

8. A measuring apparatus according to claim 2, wherein said model eye comprises first and second optical substances having said first and second surfaces, respectively, said light flux being emitted from a semiconductor laser and split by said light flux split member and guided to said model eye and said object eye, respectively, the coherent length of said semiconductor laser being 0.1 mm or less, said second optical substance including said second surface being provided an nonreflective film applied on the surface thereof.

9. A measuring apparatus including:
a model eye used for measuring a distance from a first objective surface of an object eye to be tested to a second objective surface;
an observation optical system for measuring an interference between reflected light flux from said model eye and reflected light flux from said object eye;
a light flux split member for splitting light flux and guiding coherent split light flux to said object eye and said model eye, respectively; and
an amount of light regulating optical member disposed between said light flux split member and said model eye;
said model eye being provided with a first surface corresponding to said first objective surface and a second surface corresponding to said second objective surface;
said interference fringe between said first surface and said first objective surface being observed, and said interference fringe between said second surface and said second objective surface being observed, in order to measure the length of a visual line as a distance from said first objective surface (eye axial length) to said second objective surface, the depth of the anterior chamber, the thickness of a crystal lens.

10. A measuring apparatus according to claim 9, wherein said first surface is formed in such a manner as to be in generally correspondence with the curvature of said surface of the cornea of the object eye and said second surface is formed in such a manner as to be in generally correspondence with the curvature of said surface of the retina of the object eye.

* * * * *